United States Patent [19]

Elgas

[11] Patent Number: 5,080,868
[45] Date of Patent: Jan. 14, 1992

[54] SPARGER ASSEMBLY

[76] Inventor: David H. Elgas, 4886 Cannington Dr., San Diego, Calif. 92117

[21] Appl. No.: 524,004

[22] Filed: May 16, 1990

[51] Int. Cl.$^5$ .............................................. B01L 5/00
[52] U.S. Cl. .................................... 422/99; 422/100; 261/122; 55/255; 55/256
[58] Field of Search ............... 261/122; 422/99, 100; 73/19.01, 19.1; 55/244, 255, 256

[56] References Cited

U.S. PATENT DOCUMENTS

| | | | |
|---|---|---|---|
| 3,398,935 | 8/1968 | Livesey et al. | 259/18 |
| 3,485,404 | 12/1969 | Newton | 261/122 |
| 3,740,041 | 6/1973 | Jones | 261/64 |
| 3,813,223 | 5/1973 | Fleck | 23/259 |
| 4,119,403 | 10/1978 | Rex | 23/232 |
| 4,136,970 | 1/1979 | Cabrera et al. | 336/101 |
| 4,141,312 | 2/1979 | Louder et al. | 422/99 |
| 4,344,917 | 8/1982 | Schorno | 422/78 |
| 4,565,660 | 1/1986 | Hultholm et al. | 261/121 R |
| 4,610,847 | 9/1986 | Hood et al. | 422/102 |
| 4,752,383 | 6/1988 | McKay et al. | 209/164 |
| 4,815,978 | 3/1989 | Mazza et al. | 435/4 |

Primary Examiner—Robert J. Warden
Assistant Examiner—Laura E. Collins
Attorney, Agent, or Firm—Calif Kip Tervo

[57] ABSTRACT

A sparge assembly including a integral frit can be used with a common test tube. The test tube is retained by a tube fitting on the bottom of an enclosure. An elongated purge gas tube passes through the enclosure and extends downward to terminate near the test tube bottom. The bottom end of the purge tube has a metal frit attached for discharge of received purge gas. Gas is collected from the enclosure with an outlet tube. A liquid input needle passes through the enclosure and terminates within near the test tube bottom. According to an alternate embodiment of the invention, the gas outlet tube is fitted with a bushing having an outer diameter for fitting into a host instrument's tube fitting. Preferably, the gas outlet tube exits out the top of the enclosure so that a liquid needle may pass through the gas outlet tube and into the test tube. An antifoaming test tube is made by coating the tube inside with a thin layer of antifoam agent, such as a silicone emulsion, and then baking the tube and coating to drive off any volatiles. The antiform tube is cooled and capped for later use.

12 Claims, 1 Drawing Sheet

SPARGER ASSEMBLY

BACKGROUND OF THE INVENTION

1. Field of the Invention

This invention relates in general to a fritted sparger and more specifically to a fritted sparge device capable of utilizing common test tubes. A coating of anti-foam solution on the inside of the test tubes prevents foaming.

2. Background of the Invention

It is often desirable to determine the presence and nature of volatile organic compounds in water, soil, and sludge. Such a determination is a significant part in the Environmental Protection Agency's monitoring program. Various publications, such as "Test Methods for Evaluating Solid Waste, SW-846", describe methods for making the determination. In general, the method requires placing the samples (aqueous samples or soil-/water dispersions) in sparging vessels and passing high purity gas bubbles through the samples. The high purity gas bubbles collect the organic vapor and carry it to an absorption tube that concentrates the vapor for subsequent thermal desorption and analysis by gas chromatography. The Environmental Protection Agency requires that these sparging vessels meet requirements for bubble size, location of bubble origination, and the ability to be heated.

Commercial purge and trap analytical instruments use several types of vessels for holding the sample during sparging. The most common vessel is a specially blown glass tube containing a frit fused into the bottom (hereinafter a "bottom fritted sparger"). Purge gas is introduced into the bottom of the vessel through the frit. Another method of sparging uses a glass cylinder vessel, such as a common test tube, for retaining the sample. A narrow needle inserted into the test tube and terminating near the bottom is used to induce purge gas into the sample. This is called a needle sparger.

During sparging, the gas passes through the frit as a fine bubble froth or through the needle as a line of bubbles. Where practical (see below) fritted sparging produces the most favorable action and results.

A common (and EPA required) method of inducing samples to the vessel is by use of an induction needle, which, in a needle sparger, may be the same needle with appropriate valving. With appropriate valving, this same induction needle may be used to drain the sample from the vessel.

At their interface with the sparging vessel, conventional purge and trap analysis devices provide a source of purge gas and means for introducing it to the sample (i.e. the needle sparger or glass frit), include a tube fitting means for enclosing the top of the vessel including means for collecting the gas emitted from the vessel, and include an induction needle usually passing through the top enclosure.

Bottom fritted spargers are expensive ($50–$90 at present) and are easily broken. Keeping a supply on hand to allow for breakage ties up many hundreds of dollars. Exacerbating this money problem, is the fact that different vessels are required by various analyzer manufactures. Thus, several inventories may be required.

Bottom fritted spargers must be cleaned between samples that have an oily, soapy, or silty character. The cleaning requires solvents, high purity water, and oven baking. Additionally, cleaning is quite time consuming and increases the likelihood of breakage.

Use of a multiple array autosample analyzer dictates that some samples sit in the vessel for a long period of time. The long contact time causes settling and the sample may clog the frit which may prevent successful sparging. This often occurs with common soil/water samples.

Needle spargers allow use of common disposable test tubes. Needle spargers are not as subject to clogging as are bottom fritted spargers. However, even needle spargers are subject to clogging when samples, such as soil samples, sit for more than an hour, such as in a multiple array autosampler. Also, when the test tube containing the sample is inserted into the tube fitting, the needle often cores the soil sample and clogs as result.

Frequent switching between bottom fritted spargers and needle spargers is common but time consuming. In addition to the obvious hardware manipulation, it requires increased recalibration steps.

Another method uses a fritted glass dip tube in place of a needle sparger. Common disposable test tubes can be used with this method. The large diameter required of the fritted glass dip tube precludes the use of the smaller (and cheaper) test tubes because the dip tube takes up a great portion of the volume. The large bore of the glass dip tube, its hyrophobic nature, and its inherently large porosity combine to lead to backfilling of the tube upon standing. When very small particles of soil are present, the tube tends to clog and the resulting backpressure prevents successful sparging. Backfilling may lead to cross contamination. Conventionally, the fritted dip tube replaces the induction needle. Hence, one must fill the test tube with a liquid sample before attaching the test tube to the analyzer. This promotes ambient contamination, loss of very volatile constituents, and violates EPA protocol. Special fittings are required to switch between use of the fritted glass dip tube and normal bottom fritted spargers.

Laboratory throughput is greatly increased by automatic sparger filling from a multiple vial sampler. This technique requires an automatic sparger drain feature which is not usable with either needle spargers or a fritted drip tube.

Therefore, it is desirable to have an improved sparging apparatus for purging and trapping which overcomes the shortcomings of the conventional art.

It is particularly preferable that the sparging assembly utilize common disposable test tubes.

SUMMARY OF THE INVENTION

According to the invention, a sparge assembly that includes a integral frit can be used with a common test tube. The test tube is retained by a tube fitting on the bottom of an enclosure. An elongated purge gas tube passes through the enclosure and extends downward to terminate near the test tube bottom. The bottom end of the purge tube has a metal frit attached for discharge of received purge gas. Gas is collected from the enclosure with an outlet tube.

The assembly may include liquid input needle passing through the enclosure and terminating within the test tube near the test tube bottom.

According to an alternate embodiment of the invention, the gas outlet tube is fitted with a bushing having an outer diameter for fitting into a host instrument's tube fitting. Preferably, the gas outlet tube exits out the top of the enclosure so that a liquid input needle may pass through the gas outlet tube and into the test tube.

An antifoaming test tube is made by coating the tube inside with a thin layer of antifoam agent, such as a silicone emulsion, and then baking the tube and coating to drive off any volitiles. The antifoam tube is cooled and capped for later use.

Other features and many attendant advantages of the invention will become more apparent upon a reading of the following detailed description together with the drawings, in which like reference numerals refer to like parts throughout.

DETAILED DESCRIPTION OF THE INVENTION

Figure 1:
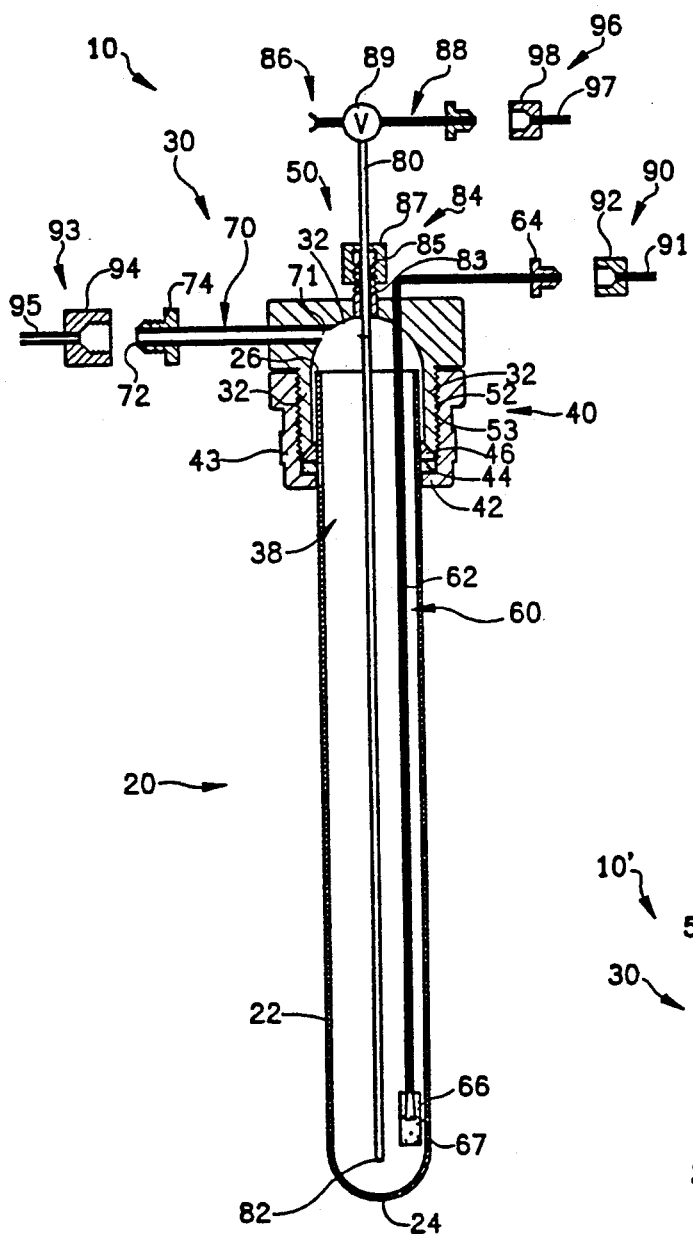
FIG. 1 is a half-sectional view of a preferred embodiment of the sparge assembly of the present invention.

With reference now to the drawing, and more particularly to FIG. 1 thereof, there is shown a preferred embodiment of the sparger assembly, denoted generally as 10, of the present invention in half-sectional view and also shown is some of the common apparatus for connecting the sparger assembly to a purge and trap analysis system.

A purge and trap analysis system includes a source of purge gas, denoted generally as 90 and represented in FIG. 1 as connector tube 91 and tube fitting connector 92, and an output gas reception port, denoted generally as 93 and represented here as tube fitting connector 94 and tube 95. Preferably the analysis system also provides a drain port, denoted generally as 96 and represented here as drain tube 97 and fitting connector 98, for draining samples from the sparging vessel.

Sparging vessel, test tube 20, shown is of the common inexpensive disposable variety having a circular cylindrical side wall 22, a closed bottom end 24, and an open top end 26. Although a particular type of test tube is shown, it will be seen that the invention is operable with a variety of test tube shapes and is not restricted to that shown in the drawing.

Sparge assembly 10 includes a test tube top end enclosure, denoted generally as 30, for attachment to test tube open top end 26 including a cap, denoted generally as 50, and walls 32 surrounding the enclosure interior. Enclosure 30 encloses the test tube top open end 26 and has a bottom orifice 38 for receiving test tube top open end 26.

Enclosure 30 includes test tube retaining and sealing means, such as a tube fitting, denoted generally as 40, for retaining top end 26 of test tube 20 in enclosure 30 such that test tube top open end 26 is in fluid communication with the enclosure interior and for sealing engaging around test tube 20 to prevent venting from the enclosure around the tube 20. In the preferred embodiment shown the tube fitting 40 includes standard bottom elements such as coupling nut 42 retaining plastic grip ring 44 and plastic sealing cone 46. Coupling nut 42 includes an internally threaded upper portion 43. The lower portion 52 of cap 50 serves as the fitting sleeve and includes threads 53 for mating with threads 43 on coupling nut 42. When threads 43 and 53 are only partially engaged, the upper end of a test tube may be inserted in bottom orifice 38. Further engaging threads 43,53 causes sealing cone 46 and grip ring 44 to press against test tube 20 and retain it in enclosure 30 and seal around it.

Tube fitting 40 including enclosure cap lower portion 52 is proportioned to accommodate the test tube size to be used. A common five-eighths inch tube fitting work well with sixteen millimeter disposable test tubes intended for five to 10 cc. samples.

Purge gas input means, such as fritted tube, denoted generally as 60, includes a small diameter tube 62 which passes thru cap 50 in sealed relationship therewith and extends to near the bottom of the test tube where it terminates in a small porous frit 66. Tube 62 is sufficiently flexible so that it may be easily bent to position frit 66 near the side wall or central axis of test tube 20 as desired. Connector 64 attaches purge gas tube 62 to mating connector 92 of purge gas source 90. Frit 66 has an effective porosity within the range of 2 to 200 microns. However, a porosity range of 5 to 50 microns is preferable and a porosity of 10 microns is optimum for general use. The frit is 0.10 to 0.50 inches in length and has a blind bore 67. Purge gas tube 62 is attached to the beginning of bore 67 by any suitable means, preferably by soldering. A typical frit is 0.125 inches in diameter and 0.3 inches long. A metal frit is hydrophobic, and water will not ordinarily back up into one of small porosity such as 10 microns.

To meet EPA standards, frit 66 must expel gas bubbles within 0.19 inches of test tube bottom 24. Although this can be accomplished with frits of different shapes than that shown, the simple small cylindrical frit in a vertical position works well.

Gas outlet means is a pathway for gas/vapor to leave the test tube and enter the host purge instrument. Gas outlet means includes gas outlet tube 70 which provides fluid communication through cap 50 with the inside of the enclosure. Inner end 71 is in fluid communication with the test tube open upper end and outer end 72 is connected to output gas reception port 93 by use of connector 74. Gas outlet tube internal diameter is 0.06 to 0.5 inches and its length is sufficient to connect to the host instrument's connecting fitting. Preferably, gas outlet tube 70 is composed of an inert material, such as stainless steel, glass, or glass-lined steel.

A liquid input means, such as hollow needle 80, allows liquid to be induced into the test tube and may also be used to drain the tube. Needle 80 passes through cap 50 in sealed relationship with enclosure 30 and terminates at lower end 82 near test tube bottom 24. Needle 80 may be of any desirable length so as to terminate near the bottom of attached test tube 20. Preferably, means, such as needle tube fitting 84, is included for adjusting the length of needle 80 inside of enclosure 30 while still maintaining a sealed relationship. Needle tube fitting 84 includes sleeve 83, sealing cone 85, and nut 87. Fritted tube 60 could also pass through cap 50 by use of a similar tube fitting.

At its upper end outside of enclosure 30, needle 80 has means for receiving fluid. In the drawing, the fluid input port is a syringe receptor 86. The upper end of needle 80 also may be connected via an alternate port 88 to a drain port 96 for removal of fluid from test tube 22. Valving means 89, such as a simple hand valve V determines whether needle 80 is in fluid communication with the fluid input port 86 or drain port 96.

The above-described sparge device is extremely versatile and is applicable to most sparging requirements. It saves time and expense.

In typical use, the upper end 26 of a clean test tube 22 is inserted in enclosure bottom orifice 38 and coupling nut 42 is tightened to retain and seal the test tube. Test fluid is induced through port 86 and valve 89 is positioned so that the fluid is induced out needle bottom end 82 into the bottom of test tube 22. Purge gas is input from port 90 through fritted tube 60 and out frit 66 and bubbles up the tube. Gas/vapor escaping from the test tube passes out port 70 for analysis. Upon completion, valve 89 may be positioned so that the liquid may be drained for collection or for re-use of the test tube or tube fitting 40 can be loosened and test tube 22 discarded.

Sparge device 10 may be used as a needle sparger by connecting purge gas source 90 to needle port 88 and capping fritted tube connector 64.

Figure 3:
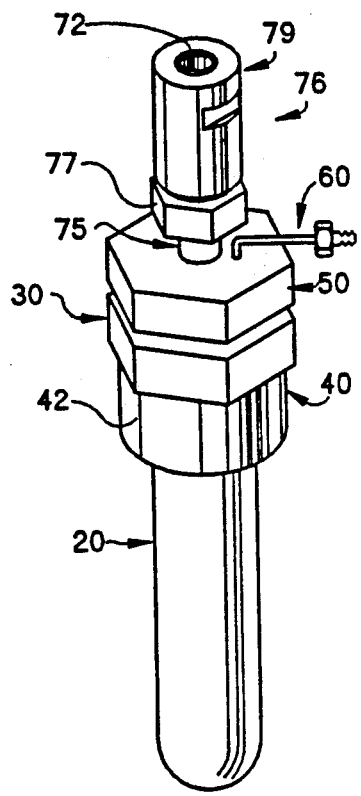
FIG. 3 is a perspective view of the sparge assembly of FIG. 2.
Figure 2:
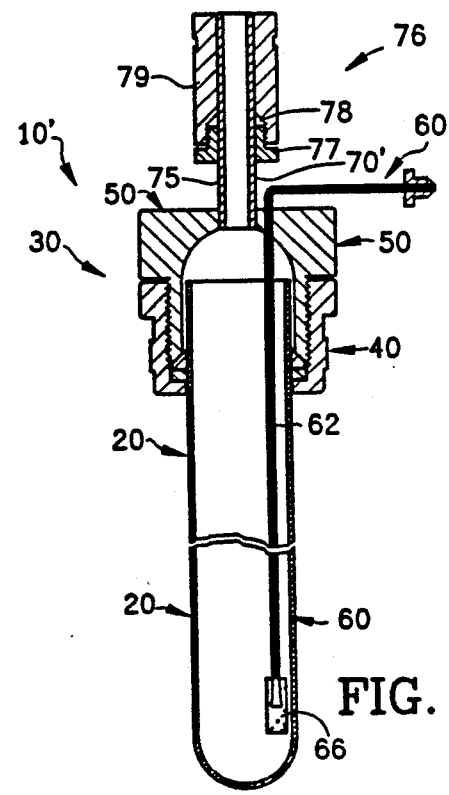
FIG. 2 is a similar half-sectional view of an alternate sparge assembly embodiment including a adapter bushing to allow use with purge and trap analyzers currently on the market.

FIGS. 2 and 3 illustrate an alternate embodiment, denoted generally as 10', of the sparge device of the invention designed for use with host analysis instruments which have a test tube fitting for mounting the test tube. Sparge device 10' is particularly configured to instruments also having a liquid input needle. FIG. 2 is a half-sectional view similar to that of FIG. 1. FIG. 3 is a perspective view.

Sparge device 10' is very similar to that of FIG. 1 in that it includes enclosure 30 accommodating fritted tube 60 and including tube fitting 40 holding common disposable test tube 22. However, gas outlet means 70' is a rigid tube 75 which passes through the top of cap 50. Output tube 75 may be of an outer diameter so as to directly mount in a tube fitting of the host instrument or may include an adapter bushing, denoted generally as 76, to allow it to fit into a variety of tube fitting sizes of various host instrument manufacturers.

Adapter bushing 76 is similar to a tube fitting and includes internal sleeve nut 77 having external threads, outer bushing 79 having a cylindrical outer sleeve/-bushing 79 of diameter to fit the host instrument's tube fitting, and sealing cone 78 for sealing between tube 75 and outer bushing 79. A different diameter bushing 79 is required for each size host instrument tube fitting. In this manner, the purge device 10' is adaptable to all host instruments having tube fittings.

Purge device 10' will also fit onto host instruments having a liquid input needle that projects into the retained sparge vessel. Because gas outlet tube 75 is axially aligned with test tube 22, the needle can pass through gas outlet tube 75 into test tube 22. In this configuration, purge device 10' functions exactly in the same manner as purge device 10.

The fritted sparger device described above is particularly efficient when used in conjunction with an antifoaming test tube for prevention of foam during the purging process.

An antifoaming test tube is made by coating the inner surface of a test tube with an antifoam agent as a water emulsion having two to seventy percent solids. A typical antifoam agent is a silicone emulsion containing a silicone fluid, glycerol monosterarate, and water which may be applied in a thin coat to the test tube inside surface by any effective means, such as by use of a cotton or foam swab. Brushing, spraying, or rinsing may also be used to apply various antifoam agents.

The test tube is then baked in an oven for a period of time sufficient to remove all volatile impurities. For the silicone emulsion mentioned, a typical baking cycle would be twenty minutes at one hundred twenty degrees Celsius. Preferably, all impurities that are a natural part of the manufacturing process must be sufficiently volatile to be removed by baking in a one hundred fifty degree Celsius oven. After baking the antifoam must retain its ability to redisperse in the water sample and also destroy any foam created during the purging process.

The baked tube is cooled and is capped to maintain cleanliness. Antifoam test tubes prepared in this manner have been successfully used with soapy water, sewage, soapy soils, carbonated beverages, and oily emulsions.

It can be seen that the sparge assembly of the present invention results in improved purging and in time and cost efficiencies over conventional devices. Low cost disposable test tubes can be used and these may be quickly and easily removed and replaced. For clean water samples, the test tube can be left in place and the sample removed using the drain feature. The sparge assembly can be used as either a frit sparger or a needle sparger by simply switching the purge gas line. The configuration of FIG. 2 may be used with any host instrument without modification of the host instrument. This allows quick and simple removal of the sparge assembly and reversion to the prior methods and apparatus if desired for any reason.

The foregoing has been descriptions of exemplary embodiments of a sparge assembly which is constructed in accordance with the principles of this invention. Although particular embodiments of the invention have been illustrated and described, various changes may be made in the form, construction, and arrangement of the parts without sacrificing any of its advantages. For example, the gas outlet tube 70 of FIG. 1 could be disposed as the tube 70' in FIG. 2 with the needle 80 passing axially where the tube 70 departs cap 50. In this configuration, needle 80 sealing departs gas output tube 70 above cap 50. Also, for example, although a common tube fitting has been shown as a tube retaining and sealing means, other devices are available which accomplish a similar effect.

Therefore, it is to be understood that all matter herein is to be interpreted as illustrative and not in any limiting sense, and it is intended to cover in the appended claims such modifications and changes as come within the true spirit and scope of the invention.

I claim:

1. A sparge assembly comprising:
   a test tube having:
      a bottom; and
      a top end having an exterior annular wall and a top end orifice;
   a test tube top enclosure for attachment to said test tube open top end comprising:
      walls defining an enclosure including:
         an interior;
         a bottom orifice for receiving said test tube open top end; and
         tube fitting means for removably retaining said test tube in said enclosure bottom orifice and for circumferentially sealing engaging said test tube top end exterior annular wall independent of pressure within said test tube such that said test tube top end orifice is in sealed fluid communication with said enclosure interior;
   purge gas input means comprising elongated tube means passing in sealed relationship through said test tube top enclosure wall and having outer end external to said enclosure for receiving purge gas and extending downward through said enclosure bottom orifice and having a lower end terminating near said test tube bottom and having a frit attached to said tube lower end for discharge of received purge gas;

gas outlet means passing through said test tube top enclosure wall including an outer end external to said enclosure for providing fluid communication between said test tube top orifice and said gas outlet means outer end; and liquid input needle means passing in sealed relationship through said test tube top enclosure wall including a top end external to said test tube top enclosure and a bottom end terminating within said test tube near said test tube bottom for providing for fluid communication therebetween.

2. The sparge assembly of claim 1 wherein:
said liquid input needle means includes:
a liquid input needle including:
a top end external to said test tube top enclosure; and
a bottom end within said test tube; and
further including:
input needle adjustment means for adjusting the length of the portion of said liquid input needle passing through said test tube top enclosure wall.

3. The sparge assembly of claim 2 wherein:
said liquid input needle adjustment means is a tube fitting integral with said test tube top enclosure wall.

4. The sparge assembly of claim 2 further including:
valving means connected to said liquid input needle means top end including a fluid input port and an alternate port for selectively placing either said fluid input port or said alternate port in fluid communication with said liquid input needle.

5. The sparge assembly of claim 1 wherein:
said frit is metal.

6. The sparge assembly of claim 1 wherein:
said frit is made of hydrophobic material.

7. The sparge assembly of claim 1 wherein:
said frit is metal with an effective porosity of 5 to 50 microns.

8. A sparge assembly comprising:
a test tube having:
a bottom; and
a top end having an exterior annular wall and a top end orifice;
a test tube top enclosure for attachment to said test tube open top end comprising:
walls defining an enclosure including:
an interior;
a bottom orifice for receiving said test tube open top end; and
tube fitting means for removably retaining said test tube top end in said enclosure bottom orifice and sealing engaging said test tube top end exterior annular wall independent of pressure within said test tube such that said test tube top end orifice is in sealed fluid communication with said enclosure interior;
purge gas input means comprising elongated tube means passing in sealed relationship through said test tube top enclosure wall and having outer end external to said enclosure for receiving purge gas and extending downward through said enclosure bottom orifice and having a lower end terminating near said test tube bottom end and having a frit attached to said tube lower end for discharge of received purge gas;
gas outlet means passing upward through said test tube top enclosure wall including an outer end external to said enclosure for providing fluid communication between said test tube top orifice and said gas outlet means outer end; said gas outlet means comprising a vertical passage such that a liquid input needle can be inserted for terminating in the proximity of said test tube bottom.

9. The sparge assembly of clam 8 further comprising:
bushing means including a bushing and means for sealingly attaching said bushing to said gas outlet means; said bushing having an outer diameter for fitting into a host instrument's tube fitting.

10. The sparge assembly of claim 8 wherein:
said frit is metal.

11. The sparge assembly of claim 8 wherein:
said frit is made of hydrophobic material.

12. The sparge assembly of claim 8 wherein:
said frit is metal with an effective porosity of 5 to 50 microns.

* * * * *